(12) United States Patent
Wieser

(10) Patent No.: US 11,857,224 B2
(45) Date of Patent: Jan. 2, 2024

(54) BONE PLATE

(71) Applicant: Innovasis, Inc., Salt Lake City, UT (US)

(72) Inventor: Eric Wieser, West Lake, TX (US)

(73) Assignee: Innovasis, Inc., Salt Lake City, UT (US)

( * ) Notice: Subject to any disclaimer, the term of this patent is extended or adjusted under 35 U.S.C. 154(b) by 14 days.

(21) Appl. No.: 16/916,814

(22) Filed: Jun. 30, 2020

(65) Prior Publication Data

US 2020/0405358 A1    Dec. 31, 2020

Related U.S. Application Data

(60) Provisional application No. 62/868,965, filed on Jun. 30, 2019, provisional application No. 62/868,967, filed on Jun. 30, 2019.

(51) Int. Cl.
| | |
|---|---|
| *A61B 17/70* | (2006.01) |
| *A61F 2/44* | (2006.01) |
| *A61F 2/30* | (2006.01) |
| *A61B 17/80* | (2006.01) |
| *A61B 17/72* | (2006.01) |

(Continued)

(52) U.S. Cl.
CPC ...... *A61B 17/7059* (2013.01); *A61B 17/8057* (2013.01); *A61F 2/30749* (2013.01); *A61F 2/4455* (2013.01); *A61B 17/7061* (2013.01); *A61B 17/7258* (2013.01); *A61B 17/7275* (2013.01); *A61B 17/8052* (2013.01); *A61B 17/8061* (2013.01); *A61B 17/844* (2013.01); *A61B 17/863* (2013.01); *A61B 17/864* (2013.01); *A61B 17/8625* (2013.01)

(58) Field of Classification Search
CPC ............ A61B 17/8042; A61B 17/7059; A61B 17/8057; A61B 17/7061; A61B 17/80; A61B 17/8033; A61B 17/8047; A61B 17/8052; A61B 17/8061; A61B 17/8665; A61B 17/8695; A61B 2017/867; A61B 17/8655; A61B 17/8625; A61B 17/863; A61B 17/7258; A61B 17/7275; A61B 17/844; A61B 17/84; A61F 2/30749; A61F 2/4455
USPC ....... 606/286, 288–290, 305, 310, 313, 319, 606/320, 326–327, 314, 316, 280
See application file for complete search history.

(56) References Cited

U.S. PATENT DOCUMENTS

| | | | | |
|---|---|---|---|---|
| 6,017,345 | A * | 1/2000 | Richelsoph | ........ A61B 17/7059 606/291 |
| 6,261,291 | B1 * | 7/2001 | Talaber | .............. A61B 17/8042 606/295 |

(Continued)

OTHER PUBLICATIONS https://www.manufacturingtomorrow.com/article/2017/07/understanding-screw-threading/10073, last accessed on Dec. 3, 2021 (Year: 2017).*

*Primary Examiner* — Marcela I. Shirsat
(74) *Attorney, Agent, or Firm* — Brooks, Cameron & Huebsch, PLLC

(57) ABSTRACT

A bone plate that includes apertures for bone screws and locking screws is disclosed. The locking screws can be in an aperture adjacent to the locking screw aperture such that when the locking bone screws and locking screws are in place, the head of the locking screw at least partially covers the head of the bone screw. In another example, the locking screw aperture is threaded, and the locking screw is placed on top of the bone screw.

16 Claims, 3 Drawing Sheets

(51) Int. Cl.
*A61B 17/84* (2006.01)
*A61B 17/86* (2006.01)

(56) References Cited

U.S. PATENT DOCUMENTS

| | | | | |
|---|---|---|---|---|
| 6,579,290 | B1 * | 6/2003 | Hardcastle | A61B 17/8685 |
| | | | | 606/247 |
| 8,574,271 | B2 * | 11/2013 | Crainich | A61B 17/8052 |
| | | | | 411/533 |
| 2002/0068938 | A1 * | 6/2002 | Jackson | A61B 17/7032 |
| | | | | 606/265 |
| 2002/0151899 | A1 * | 10/2002 | Bailey | A61B 17/7059 |
| | | | | 606/256 |
| 2003/0093082 | A1 * | 5/2003 | Campbell | A61B 17/8875 |
| | | | | 606/104 |
| 2003/0187442 | A1 * | 10/2003 | Richelsoph | A61B 17/8042 |
| | | | | 606/70 |
| 2004/0039387 | A1 * | 2/2004 | Gause | A61B 17/1735 |
| | | | | 606/86 B |
| 2004/0254581 | A1 * | 12/2004 | Leclair | A61B 17/8625 |
| | | | | 606/313 |
| 2013/0072990 | A1 * | 3/2013 | Simonson | A61B 17/8625 |
| | | | | 606/301 |

* cited by examiner

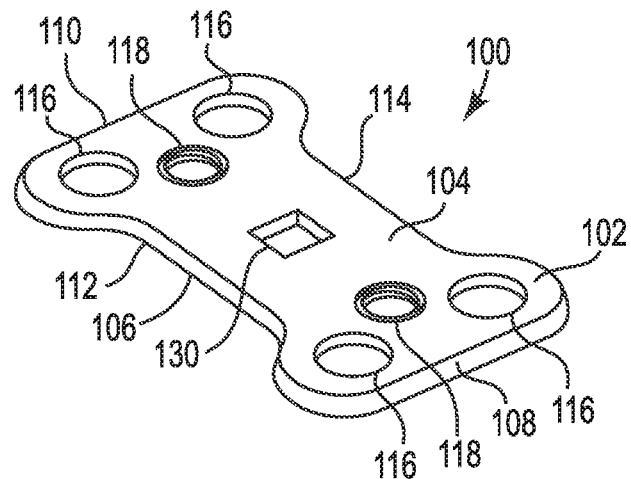
Fig. 1A
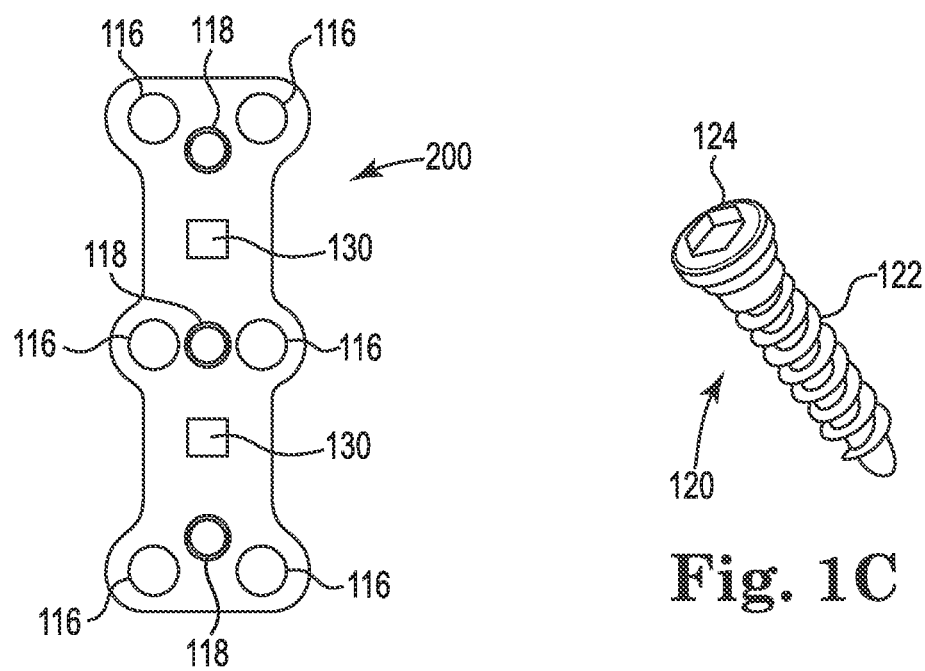
Fig. 1B
Fig. 1C

BONE PLATE

PRIORITY INFORMATION

This application claims priority of U.S. Provisional Application Ser. No. 62/868,967, filed on Jun. 30, 2019, and U.S. Provisional Application Ser. No. 62/868,965, filed on Jun. 30, 2019, the contents of which are incorporated herein by reference.

TECHNICAL FIELD

The present disclosure relates to interbody implants and, more specifically, to spinal fusion implants (e.g., cervical and/or lumbar spinal fusion implants) having locking screws for selectively locking bone screws.

BACKGROUND

The spinal column is made up of spaced apart vertebra that are each separated by a cushioning disc. If a disc ruptures or is otherwise damaged, the adjacent vertebra can press against the spinal cord which can cause pain and loss of mobility. In one approach to treating a damaged disc, at least a portion of the damaged disc is removed, and a spinal fusion implant is inserted between the adjacent vertebrae. The implant keeps the vertebrae separated to prevent the vertebrae from pressing on the spinal cord. Eventually, the adjacent vertebrae fuse together about the implant so as to preclude any movement between the vertebrae.

The neck region of the spine is known as the cervical spine. This region consists of seven vertebrae, which are abbreviated C1 through C7 (top to bottom). These vertebrae protect the brain stem and the spinal cord, support the skull, and allow for a wide range of head movement. The first cervical vertebra (C1) is called the Atlas. The Atlas is ring-shaped, and it supports the skull. C2 is called the Axis. It is circular in shape with a blunt peg-like structure (called the Odontoid Process or "dens") that projects upward into the ring of the Atlas. Together, the Atlas and Axis enable the head to rotate and turn. The other cervical vertebrae (C3 through C7) are shaped like boxes with small spinous processes (finger-like projections) that extend from the back of the vertebrae. The thoracic spine is the center part of the spine. It is made up of 12 vertebrae. The lumbar spine is the lower portion of the spine. It is usually made up of five vertebrae, however, some people may have six lumbar vertebrae.

To help fuse the vertebrae together, the implant is formed with a hollow cavity that is manually filled with a bone growth material, such as bone allograft, prior to insertion between the vertebrae. The openings on the implant enable the bone allograft to facilitate bone growth between the vertebrae.

To help keep the implant properly positioned and stationary as the adjacent vertebrae are fusing together, bone screws are passed through the implant and are screwed into the adjacent vertebrae. One risk associated with using bone screws is that through movement of the patient, the bone screws can work loose and back out of the implant. The movement of the bone screws can cause the implant to become loose and prevent proper fusing between the vertebrae. In addition, the loose bone screw becomes a risk to the patient as it can create obstructions or damage surrounding bone or tissue.

Various approaches have been used to help lock bone screws to spinal implants. Such approaches, however, have typically suffered from shortcomings such as being ineffective, difficult to use, or having a relatively high risk that all or a portion of the implant will dislodge within the patient. Accordingly, what is needed in the art are spinal implants having improved assemblies and methods for locking bone screws to the implant.

BRIEF DESCRIPTION OF THE DRAWINGS

FIG. 1A is a perspective view of a bone plate in accordance with one or more embodiments of the present disclosure.

FIG. 1B is a perspective view of a bone plate in accordance with one or more embodiments of the present disclosure.

FIG. 1C is a perspective view of a bone screw in accordance with one or more embodiments of the present disclosure.

DETAILED DESCRIPTION

Figure 1D:
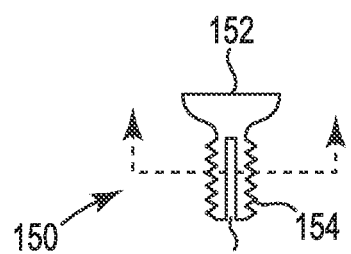
FIG. 1D is a side view of a locking screw in accordance with one or more embodiments of the present disclosure.

This disclosure relates to a bone plate for vertebral (e.g., cervical and/or lumbar) fusion. Cervical bone plates are generally placed in an anterior position on the cervical vertebra and held in place with bone screws. Lumbar bone plates are generally placed in a lateral position on the lumbar vertebra and held in place with bone screws. A locking mechanism is used to keep the bone screws from backing out after implant.

In some embodiments, the locking mechanism is in the form of a screw that is quickly and easily installed by a surgeon. The locking screw can be positioned adjacent to the one or more screw(s) that attach the cervical bone plate to each vertebral bone. In some embodiments, the locking mechanism is in the form of a screw that is quickly and easily installed by a surgeon. The head of the locking screw is of sufficient size that it lays over or partially covers the bone screw, to prevent the bone screw from backing out. The locking screw is removable if necessary.

In some embodiments, the locking mechanism is in the form of a screw that is quickly and easily installed by a surgeon and is also easily removed in the event that that is easily insertable into an opening above the bone screw to prevent the bone screw from backing out. The locking screw is removable if necessary.

In some embodiments, the locking screw comprises a shaft and threads, and has a partially open shaft which allows for the threads and shaft to have a variable diameter where the threads and shaft can be forced inward to assume a smaller outside diameter. A radial inward force applied to the screw can cause the screw to assume a smaller diameter. When no force is applied, the screw can assume its standard diameter.

In some embodiments, the threads on the locking screw have a slight upward slant. This slant can allow for less force being needed to force the screw into the bone plate shaft. It will also help prevent the screw from being pushed out of the opening in the bone plate.

In some embodiments, the locking screw has a thread direction that is opposite of the bone screw. For instance, a bone screw may have right handed threads, meaning that rotating the screw to the right (e.g., clockwise) causes it to advance and rotation to the left (e.g., counterclockwise) causes the screw to retract. In such cases, if the bone screw has right handed threads, the locking screw can have left handed threads. In the event that the bone screw begins to come out of the bone, the left-handed rotation will not cause the locking screw to back out.

In some embodiments, the bone screw locking mechanism includes a snap ring. Such embodiments may include a tool to open the snap ring.

In some embodiments, the bone screw locking mechanism is a resilient band, connected to the bone plate, that is placed over the bone screw.

Before describing various embodiments of the present disclosure in detail, it is to be understood that this disclosure is not limited to the parameters of the particularly exemplified implants, methods, systems and/or products, which may, of course, vary. Thus, while certain embodiments of the present disclosure will be described in detail, with reference to specific configurations, parameters, features (e.g., components, members, elements, parts, and/or portions), etc., the descriptions are illustrative and are not to be construed as limiting the scope of the claimed disclosure. In addition, the terminology used herein is for the purpose of describing the embodiments and is not necessarily intended to limit the scope of the claimed disclosure.

Unless defined otherwise, all technical and scientific terms used herein have the same meaning as commonly understood by one of ordinary skill in the art to which the present disclosure pertains.

Various aspects of the present disclosure, including implants, systems, processes, and/or products may be illustrated with reference to one or more embodiments or implementations, which are exemplary in nature. As used herein, the terms "embodiment" and "implementation" mean "serving as an example, instance, or illustration," and should not necessarily be construed as preferred or advantageous over other aspects disclosed herein. In addition, reference to an "implementation" of the present disclosure or disclosure includes a specific reference to one or more embodiments thereof, and vice versa, and is intended to provide illustrative examples without limiting the scope of the disclosure, which is indicated by the appended claims rather than by the following description.

As used throughout this application the words "can" and "may" are used in a permissive sense (i.e., meaning having the potential to), rather than the mandatory sense (i.e., meaning must). Additionally, the terms "including," "having," "involving," "containing," "characterized by," as well as variants thereof (e.g., "includes," "has," and "involves," "contains," etc.), and similar terms as used herein, including the claims, shall be inclusive and/or open-ended, shall have the same meaning as the word "comprising" and variants thereof (e.g., "comprise" and "comprises"), and do not exclude additional, un-recited elements or method steps, illustratively.

It will be noted that, as used in this specification and the appended claims, the singular forms "a," "an" and "the" include plural referents unless the context clearly dictates otherwise. Thus, for example, reference to a "locking screw" includes one, two, or more locking screws.

As used herein, directional terms, such as "top," "bottom," "left," "right," "up," "down," "upper," "lower," "proximal," "distal," "vertical," "horizontal" and the like are used herein solely to indicate relative directions and are not otherwise intended to limit the scope of the disclosure and/or claimed disclosure.

Various aspects of the present disclosure can be illustrated by describing components that are bound, coupled, attached, connected, and/or joined together. As used herein, the terms "bound," "coupled", "attached", "connected," and/or "joined" are used to indicate either a direct association between two components or, where appropriate, an indirect association with one another through intervening or intermediate components. In contrast, when a component is referred to as being "directly bound," "directly coupled", "directly attached", "directly connected," and/or "directly joined" to another component, no intervening elements are present or contemplated. Furthermore, binding, coupling, attaching, connecting, and/or joining can comprise mechanical and/or chemical association.

To facilitate understanding, like reference numerals (i.e., like numbering of components and/or elements) have been used, where possible, to designate like elements common to the figures. Specifically, in the exemplary embodiments illustrated in the figures, like structures, or structures with like functions, will be provided with similar reference designations, where possible.

Specific language will be used herein to describe the exemplary embodiments. Nevertheless, it will be understood that no limitation of the scope of the disclosure is thereby intended. Rather, it is to be understood that the language used to describe the exemplary embodiments is illustrative only and is not to be construed as limiting the scope of the disclosure (unless such language is expressly described herein as essential). Furthermore, multiple instances of an element and or sub-elements of a parent element may each include separate letters appended to the element number. An element label with an appended letter can be used to designate an alternative design, structure, function, implementation, and/or embodiment of an element or feature without an appended letter. Likewise, an element label with an appended letter can be used to indicate a sub-element of a parent element. However, element labels including an appended letter are not meant to be limited to the specific and/or particular embodiment(s) in which they are illustrated. In other words, reference to a specific feature in relation to one embodiment should not be construed as being limited to applications only within said embodiment.

Furthermore, multiple instances of the same element may each include separate letters appended to the element number. For example, two instances of a particular element "20" may be labeled as "20a" and "20b". In that case, the element label may be used without an appended letter (e.g., "20") to generally refer to every instance of the element; while the element label will include an appended letter (e.g., "20a") to refer to a specific instance of the element.

It will also be appreciated that where multiple possibilities of values or a range a values (e.g., less than, greater than, at least, or up to a certain value, or between two recited values) is disclosed or recited, any specific value or range of values falling within the disclosed range of values is likewise disclosed and contemplated herein.

The human spine is naturally curved. Normal lordosis is the two forward curves seen in the neck (cervical spine) and low back (lumbar spine). Normal kyphosis is the two backward curves seen in the chest (thoracic spine) and hip areas (sacral spine). Each of the naturally occurring and normal soft curves serves to distribute mechanical stress incurred as the body is at rest and during movement.

The devices disclosed herein are described in terms of treatment for the cervical spine and/or lumbar spine. In general, cervical spinal fusion is an anterior intervention, but in some instances may be lateral or posterior. In general, lumbar spinal fusion is a lateral intervention, but in some instances may be lateral or posterior. Compared to the thoracic and lumbar regions, the cervical vertebra are smaller and closer together. Compared to the cervical regions, the thoracic and lumbar vertebra are larger and farther apart.

FIG. 1A is a perspective view of a bone plate in accordance with one or more embodiments of the present disclosure. FIG. 1B is a perspective view of a bone plate in accordance with one or more embodiments of the present disclosure. Depicted in FIGS. 1A and 1B are two embodiments of bone plates incorporating features of the present disclosure. In FIG. 1A, bone plate 100 is designed to be used for stabilizing two adjacent vertebrae of a spine as part of a procedure for fusing together the adjacent vertebrae. Bone plate 100 can also be used for stabilizing a series of consecutive vertebrae for manipulation of the spine to correct spinal deformities such as scoliosis. It is appreciated that bone plate 100 and/or discrete elements thereof can also be used in other procedures for anchoring, manipulating, and/or stabilizing various bones.

Bone plate 100 comprises a main body 102 having a top surface 104 and an opposing bottom surface 106 that extend longitudinally from a proximal end 108 to a spaced apart distal end 110. Top and bottom surfaces 104 and 106 also extend laterally from a first side 112 to a spaced apart second side 114. Main body 102 can be curved in one or more directions or can be substantially planar.

A plurality of apertures 116 are formed in main body 102 that extend completely through main body 102 between top surface 104 and bottom surface 106. Each aperture 116 is designed so that the shaft 122 of a bone screw 120 can be inserted therethrough while the head 124 of the bone screw 120 is prevented from doing so. In some embodiments, aperture is countersunk so that head 124 of screw 120 is either flush with surface 104 or slightly below.

Bone screw 120 is threaded into a vertebra while head 124 biases against bone plate 100 so as to rigidly attach the vertebra to bone plate 100. Other apertures can also be included in main body 102 to aid the physician in implanting the bone plate within the body. For example, as shown in FIG. 1A, a viewing aperture 130 that passes completely through main body 102 is positioned generally centrally on the main body 102 so as to allow the physician to view the underlying spine when installing the bone plate 100. The number of viewing apertures 130 can vary. For example, in some embodiments, a single viewing aperture 130 is positioned on main body 102. In other embodiments, a plurality of viewing apertures 130 are incorporated. In other embodiments, viewing apertures 130 are omitted altogether.

The bone plate 200, shown in FIG. 1B, can be attached to three vertebrae. It is noted, however, that attachment to four, five, six, or more vertebra are within the scope of the disclosure.

In some embodiments, locking screw apertures are included in the bone plates 100 and 200. Apertures 118 can be threaded so as to receive a locking screw. FIG. 1D is a side view of a locking screw 150 in accordance with one or more embodiments of the present disclosure. Locking screw 150 includes screw head 152 and screw body 154. Screw body 154 includes slot 156 that extends the length of screw body 154 and into the interior of body 154 so as to give screw 150 a non-continuous cross section.

Figure 1E:
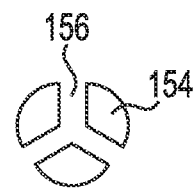
FIG. 1E is a cross-sectional view of a locking screw in accordance with one or more embodiments of the present disclosure.
Figure 1F:
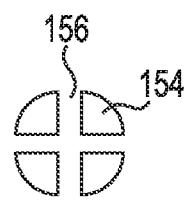
FIG. 1F is a cross-sectional view of a locking screw in accordance with one or more embodiments of the present disclosure.

FIG. 1E is a cross-sectional view of a locking screw in accordance with one or more embodiments of the present disclosure. FIG. 1F is a cross-sectional view of a locking screw in accordance with one or more embodiments of the present disclosure. As shown in FIG. 1E, slot 156 can extend to the outer surface of screw body 154 in three places. As shown in FIG. 1F, slot 156 can extend to the outer surface of screw body 154 in four places. The screw body 154 can have a variable diameter, where a radial inward pressure on the screw body 154 can cause the sections of body 154 to move radially inward, causing the body 154 to have a smaller effective diameter.

Figure 1G:
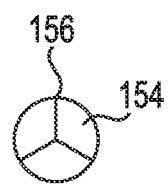
FIG. 1G is a cross-sectional view of a locking screw subject to radial pressure in accordance with one or more embodiments of the present disclosure.
Figure 1H:
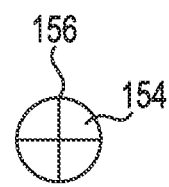
FIG. 1H is a cross-sectional view of a locking screw subject to radial pressure in accordance with one or more embodiments of the present disclosure.

FIG. 1G is a cross-sectional view of a locking screw subject to radial pressure in accordance with one or more embodiments of the present disclosure. FIG. 1H is a cross-sectional view of a locking screw subject to radial pressure in accordance with one or more embodiments of the present disclosure. When the radial pressure is released, the slots 156 in screw body 154 can reform and the cross section will again look like that shown in FIGS. 1E and 1F. While FIG. 1E shows three openings on the circumference and FIG. 1F shows four openings on the circumference, any number of slots (and thus slot openings) can be used in accordance with embodiments herein.

In some embodiments, after a surgeon has attached bone plate 100 or 200 to a vertebra, locking screw 150 can be forced into aperture 118. As the screw has a non-continuous cross section, the diameter will get smaller due to the force of screw 150 being forced into aperture 118. Once in place, the sections of screw body 154 will expand to the original diameter and the threads of screw 150 will mate with the threads of aperture 118 securing screw 150 in the aperture. The surgeon can tighten the screw by rotating head 152. Screw 150 can be unthreaded and removed from aperture 118. Aperture 118 can be placed adjacent each aperture 116 or pairs of apertures 116 and can be sized such that head 152 will partially cover head 124 of bone screw 120. In some embodiments, aperture 118 can be counter sunk so that the top of screw head 152 is at or below surface 104 even when it is over bone screw head 124.

In some embodiments, apertures 116 are threaded so as to receive a locking screw 150 that will be placed on top of bone screw 120. In such embodiments, after the surgeon has inserted bone screws 120 into plate 100 or 200, locking crews 150 can be inserted on top of bone screw 120 to keep the bone screw from backing out. In some embodiments, the locking screw can have a thread direction that is opposite the thread direction of the bone screw. For example, if the bone screw if right threaded (to advance it is turned to the right) the locking screw can be left threaded so that the left rotation that may result from the bone screw backing out will not cause the locking screw to back out. In some embodiments, plates 100 and 200 may not include locking screw apertures 118.

Figure 1I:
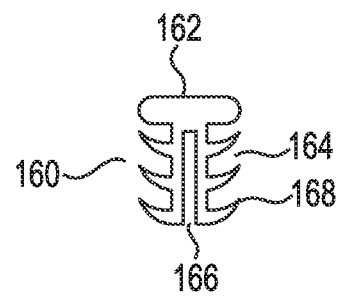
FIG. 1I is a cross-sectional view of a locking screw in accordance with one or more embodiments of the present disclosure.

FIG. 1I is a cross-sectional view of a locking screw in accordance with one or more embodiments of the present disclosure. As shown in FIG. 1I, locking screw 160 can include a head 162, screw body 164, slot 166, and threads 168. As shown, threads 168 can be pointed toward the screw head 162. The angle of the threads 168 can be from 1° to 45° away from a line perpendicular to the longitudinal axis of the screw 160. The angle of the threads 168 can be from 5° to 25° away from a line perpendicular to the longitudinal axis of the screw 160. The angle of the threads 168 can be from 10° to 20° away from a line perpendicular to the longitudinal axis of the screw 160. The upward angled threads can result in less pressure being needed to force the locking screws into aperture 116 or 118 and can reduce the chance of the screw backing out of the aperture in the event that the screw does not return to the full diameter after the radial force is released.

Figure 2A:
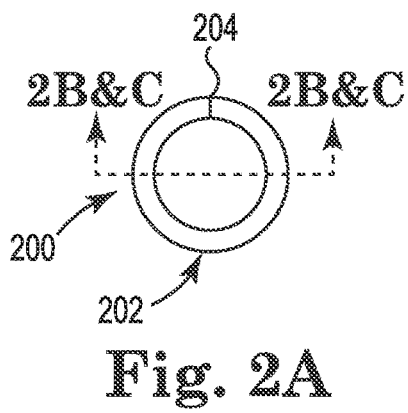
FIG. 2A is a top view of a snap ring in accordance with one or more embodiments of the present disclosure.
Figure 2B:
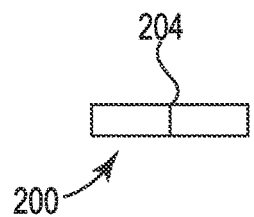
FIG. 2B is a side view of a snap ring in accordance with one or more embodiments of the present disclosure.
Figure 2C:
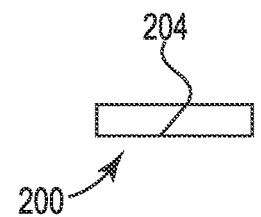
FIG. 2C is a side view of a snap ring in accordance with one or more embodiments of the present disclosure.

FIG. 2A is a top view of a snap ring in accordance with one or more embodiments of the present disclosure. Snap ring 200 has a slot 204 that allows the ring to open and attachment point 202 where the snap ring is attached to a bone plate. FIG. 2B is a side view of a snap ring in accordance with one or more embodiments of the present disclosure. FIG. 2C is a side view of a snap ring in accordance with one or more embodiments of the present disclosure. As seen in 2B and 2C, the snap ring can be described as a non-continuous ring having a vertical and/or angled slot 204.

Figure 2D:
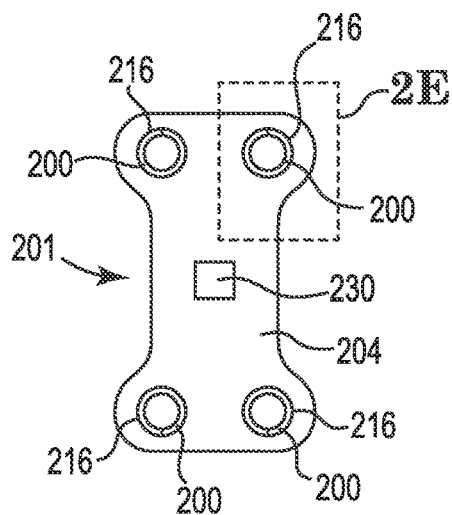
FIG. 2D is a top view of a bone plate with a snap ring in accordance with one or more embodiments of the present disclosure.
Figure 2E:
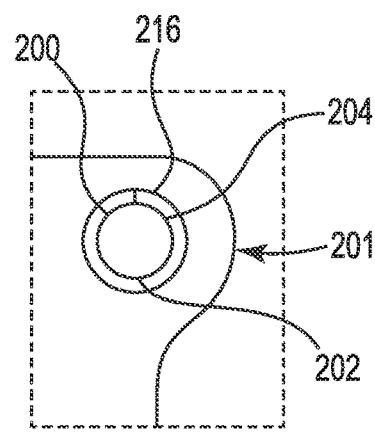
FIG. 2E is a detailed top view of a portion of a bone plate with a snap ring in accordance with one or more embodiments of the present disclosure.

FIG. 2D is a top view of a bone plate with a snap ring in accordance with one or more embodiments of the present disclosure. FIG. 2D shows bone plate 201 with snap rings 200 positioned within bone screw apertures 216. FIG. 2E is a detailed top view of a portion of a bone plate with a snap ring in accordance with one or more embodiments of the present disclosure. As shown in more detail in FIG. 2E, snap ring 200 can be positioned within aperture 216 and attached to bone plate 201 at point 202. Aperture 216 can have a diameter greater than or equal to the head of the bone screw 120 (previously described in connection with FIG. 1) plus the thickness of snap ring 200. When the surgeon installs bone screw 120 and the bottom of head 124 pushes on snap ring 200, the downward pressure of screw head 124 on the snap ring will cause slot 204 to widen. Once head 124 is beneath snap ring 200, the ring may 'snap' shut or close and hold screw 120 in place. If screw 120 is to be removed, the surgeon can pry slot 204 open with a flat instrument, causing the diameter of the ring to get larger, at which time the screw head can fit through the snap ring and the screw can be removed. In some embodiments, the bottom of head 124 can be used to help push ring 200 open.

Figure 2F:
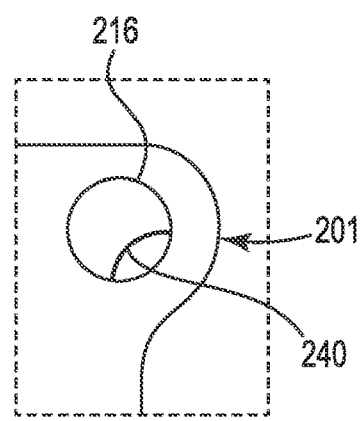
FIG. 2F is a top view of a resilient band bone screw locking mechanism in accordance with one or more embodiments of the present disclosure.

FIG. 2F is a top view of a resilient band bone screw locking mechanism in accordance with one or more embodiments of the present disclosure. As shown in FIG. 2F, a resilient band or wire 240 can be positioned in aperture 216 of plate 201. Resilient band or wire 240 can be attached at both ends to bone plate 201 with the middle section extending into the aperture 216. To install a bone screw, the surgeon can bend mechanism 240 up so that screw 120 can be inserted into the bone through aperture 216. Once the screw is installed, the surgeon can release mechanism 240 and allow it to return to its original position. Once positioned on top of screw head 124, the resilient band or wire 240 can prevent the screw from backing out. In the event that the screw needs to be removed, the surgeon can again bend the resilient band or wire 240 up and out of the way so that screw 120 can be removed.

Plates 100, 200 and 201 and screw 120, 150, and 160 can be cast, molded, milled or otherwise formed from a biocompatible material such as a polyetheretherketone (PEEK) polymer that can be reinforced with a fiber, such as carbon fiber, and/or other additives. In alternative embodiments, the plates and screws of the present disclosure can be formed from medical grade biocompatible metals (such as titanium), alloys, polymers, ceramics, or other materials that have adequate strength.

The heads of the locking and bone screws of the disclosure (124, 152, 162) can be formed with a recess to accept a tool that a surgeon may use to turn the screw. This opening can be a slot, a cross, or an opening with three, four, five, six, seven or more sides. In some embodiments, the bottom side of screw heads 124, 152, 162 can be tapered or sloped. In some embodiments, the taper of slope can match a counter sink in the screw apertures.

In some embodiments, all of the screw apertures 116 and 118 are counter sunk such that when the bone and locking screws 120, 150, 160 are inserted, the top of the screw heads are flush with surface 104.

When the bone plates described herein are used in an anterior cervical discectomy and fusion technique, an incision can be made in the front of the neck which allows the surgeon to remove the damaged and protruding disc and associated bone spurs in order to relieve any pressure on the spinal cord and nerve roots. When the bone plates described herein are used in a lateral lumbar discectomy and fusion technique, an incision can be made in the abdomen which allows the surgeon to remove the damaged and protruding disc and associated bone spurs in order to relieve any pressure on the spinal cord and nerve roots. After the disc is removed, the gap that has been created between the two bones is then typically filled with a piece of bone graft (obtained from a cadaver or from the patient's pelvis) or with a synthetic material. In some instances, the bone graft material is carried in a titanium or medical grade plastic cage device. Once the pressure on the nerves has been relieved, the goal of the procedure is to cause the two bones to grow together (called a fusion). While procedures herein have been described with respect to particular example placements (e.g., lateral, anterior, posterior), it is noted that other placements other than those specifically described may be used in accordance with embodiments herein.

For cervical applications, the term means that at least one cervical vertebra is involved. For lumbar applications, the term means that at least one lumbar or thoracic vertebra is involved.

The present disclosure may be embodied in other specific forms without departing from its spirit or essential characteristics. For example, the placement, orientation and number of bone screws and locking screws can be modified as needed. For example, in one embodiment, only two bone screws may be used and thus only one locking screw may be required.

The described embodiments are to be considered in all respects only as illustrative and not restrictive. The scope of the disclosure is, therefore, indicated by the appended claims rather than by the foregoing description. All changes which come within the meaning and range of equivalency of the claims are to be embraced within their scope.

What is claimed is:

1. An orthopedic system comprising:
   a bone plate, the bone plate comprising a top and a bottom with bone screw apertures and locking screw apertures therethrough, the locking screw apertures having threads;
   a plurality of bone screws, each of the bone screws comprising a head and a shaft;
   a plurality of locking screws, each of the locking screws comprising a head, a shaft, threads and a longitudinal axis;
   wherein each of the locking screws include a number of slots that start at a first end of the locking screws, extend through the shaft past a thread adjacent to the head of the locking screws, and terminate in a neck of the locking screws before reaching the head of the locking screws;
   wherein the bone plate apertures comprise a smaller diameter than the bone screw head;
   wherein the threads of the locking screw mate with the threads of the locking screw apertures; and
   wherein a diameter of the body of the locking screws is variable based on a radial inward force applied to the body of the locking screws when inserting the locking screws in the locking screw apertures.

2. The orthopedic system of claim 1, wherein the bone plate is a cervical bone plate.

3. The orthopedic system of claim 1, wherein the bone plate is a lumbar bone plate.

4. The orthopedic system of claim 1, wherein the threads of the locking screws are oriented toward the head of the locking screw.

5. The orthopedic system of claim 4, wherein the threads are orientated at an angle of 10° to 20° above a line perpendicular to the longitudinal axis of the locking screw.

6. The orthopedic system of claim 1, wherein the locking screws have a non-continuous cross section that is perpendicular to a longitudinal axis of the shaft of the locking screws.

7. The orthopedic system of claim 1, wherein the bone plate is configured to attach to two vertebrae.

8. The orthopedic system of claim 1, wherein the bone plate is configured to attach to three vertebrae.

9. The orthopedic system of claim 1, wherein the bone plate is configured to attach to four or more vertebrae.

10. The orthopedic system of claim 1, wherein a thread direction of the locking screws is opposite a thread direction of the bone screws.

11. An orthopedic system comprising:
    a bone plate, the bone plate comprising a top and a bottom with bone screw apertures and locking screw apertures therethrough, the locking screw apertures having threads;
    a plurality of bone screws, each of the bone screws comprising a head and a shaft;
    a plurality of locking screws, each of the locking screws comprising a head, a shaft, threads and a longitudinal axis;
    wherein each of the locking screws include a number of slots that start at a first end of the locking screws, extend through the shaft past a thread adjacent to the head of the locking screws, and terminate in a neck of the locking screws before reaching the head of the locking screws;
    wherein the bone plate apertures comprise a smaller diameter than the bone screw head;
    wherein the threads of the locking screws mate with the threads of the locking screw apertures; and
    wherein a diameter of a body of the locking screws is variable based on a number of slots in the body of the locking screws that change dimension in response to a radial inward force applied to the body of the locking screws when inserting the locking screws in the locking screw apertures.

12. The orthopedic system of claim 11, wherein a thread direction of the locking screws is opposite a thread direction of the bone screws.

13. The orthopedic system of claim 11, wherein the locking screws have a non-continuous cross section that is perpendicular to a longitudinal axis of the shaft of the locking screws.

14. The orthopedic system of claim 13, wherein the cross section of the locking screws has three openings.

15. The orthopedic system of claim 14, wherein the bone screw apertures and locking screw apertures are counter sunk.

16. The orthopedic system of claim 13, wherein the cross section of the locking screws has four openings.

* * * * *